(12) United States Patent
Politi et al.

(10) Patent No.: US 6,339,160 B1
(45) Date of Patent: Jan. 15, 2002

(54) METALLOPROTEINASE INHIBITORS, THEIR THERAPEUTIC USE AND PROCESS FOR THE PRODUCTION OF THE STARTING COMPOUND IN THE SYNTHESIS THEREOF

(75) Inventors: Vincenzo Politi; Enrico Gavuzzo; Carlo Gallina; Giovanni Di Stazio; Silvana D'Alessio; Antonio Sella; Cinzia Piazza; Cesare Giordano; Barbara Gorini; Gabriella Panini; Mario Paglialunga Paradisi; Maurizio Cirilli; Giorgio Pochetti; Fernando Mazza, all of Rome (IT)

(73) Assignees: Polifarma S.p.A.; Consiglio Nazionale Delle Ricerche, both of Rome (IT)

( * ) Notice: Subject to any disclaimer, the term of this patent is extended or adjusted under 35 U.S.C. 154(b) by 0 days.

(21) Appl. No.: 09/462,932
(22) PCT Filed: Jul. 17, 1998
(86) PCT No.: PCT/IT98/00202
§ 371 Date: May 9, 2000
§ 102(e) Date: May 9, 2000
(87) PCT Pub. No.: WO99/03878
PCT Pub. Date: Jan. 28, 1999

(30) Foreign Application Priority Data

Jul. 17, 1997 (IT) ........................................ RM97A0441

(51) Int. Cl.$^7$ ........................... C07K 5/078; A61K 38/05
(52) U.S. Cl. ........................ 548/113; 548/119; 548/414
(58) Field of Search .................. 548/414, 119; 514/80

(56) References Cited

FOREIGN PATENT DOCUMENTS

| EP | 0 401 963 | 12/1990 |
|---|---|---|
| EP | 0 758 021 | 2/1997 |
| WO | 92/06108 | 4/1992 |

OTHER PUBLICATIONS

Cirilli FEBS Lett. 418 (3) 319–322, 1997.*
Cirilli, M. et al., "2–ANG X–ray structure of adamalysin II complexed with a peptide phosphonate inhibitor adopting a retro–binding mode," FEBS Letters, 418, (1997), 319–322.
Calcagni, A. et al., "Inhibitors of zinc–dependent metallopeptidases: N–(2–furoyl)–(Z)–.alpha.,.beta.–dihydrol eucyl–L–tryptophan," IL Farmaco, 48 (9), 1271–1277; 1993.

* cited by examiner

*Primary Examiner*—Robert Gerstl
(74) *Attorney, Agent, or Firm*—Browdy and Neimark

(57) ABSTRACT

Objects of the present invention are compounds of a peptido-mimetic character having the capacity of acting as inhibitors of metalloproteinases produced by venom of snake, and of other metalloproteinases of human origin which have been put in relation with various pathologies in man, including tumoral growth and metastatization, aterosclerosis, multiple sclerosis, Alzheimer's disease, osteoporosis, hypertension, rheumatoid arthritis and other inflammatory diseases.

Object of the present invention is also the procedure for the production of diethylester of (1)-phosphotryptophan, as an initial product necessary to synthesize all compounds mentioned above.

10 Claims, No Drawings

METALLOPROTEINASE INHIBITORS, THEIR THERAPEUTIC USE AND PROCESS FOR THE PRODUCTION OF THE STARTING COMPOUND IN THE SYNTHESIS THEREOF

CROSS REFERENCE TO RELATED APPLICATION

The present application is the national stage under 35 U.S.C. 371 of PCT/IT98/00202, filed Jul. 17, 1998.

DESCRIPTION

The present invention has as its object new compounds usable in the therapy of a series of human pathologies such as tumoral growth and metastatization, atherosclerosis, multiple sclerosis, Alzheimer's disease, osteoporosis, rheumatoid arthritis and other inflammatory diseases. Said compounds in fact, following in vitro experiments extensively described in the following chapters, showed a remarkable inhibitory capability on certain human enzymes, the zinc-dependent metalloproteinases, which have been related with such pathologies (see for example: "Inhibition of matrix metalloproteinases. Therapeutic potential" - Annuals N.Y. Acad.Sci. 732 (1994)). Thus although an integration of experimental data with adequate evidence in vitro is naturally necessary, the results collected already allow to expect their usability in specific therapies. Moreover such inhibitory capacity was originally demonstrated also in a series of zinc-dependent metalloproteinases extracted from snake venoms, also denominated "hemorrhagines" for their capacity of inducing extensive internal herorrhagies in victims of snake bites, and constitute the most damaging agent in the venomous mixtures elaborated by Crotalidae and Viperidae. Thus their usability also in preparing specific antidotes against venom of Crotalidae and Viperidae seems evident.

The design and synthesis of such compounds in fact constitutes the last step in a long course of research, based on the study of the structure and action mechanism of certain particular zinc-dependent metalloproteinases called hemorhagines.

The article IL FARMACO (1993), 48 (9), 1271–7 shows that in the study of peptidic inhibitors a conformationally restricted model of compound tested on proteinase II from Crotalus Adamanteus snake venom has a sensibly lower inhibitory activity than that of related substrates. This result indicates that the structure of the inhibitor compound has direct influence on the fitting and bind at the enzyme active site and is not foreseeable a priori.

The so-called Hemorrhagic Factors of Hemorrhagines constitute a very important class of enzymes detected in the venom of snakes belonging to the Crotalidae family. They are structurally of use to the snake as they rapidly induce extended internal hemorrhagies in victims, causing circulatory collapse and preventing the victim from escaping its fate. The mechanism of the hemorrhagic action is due to the particular ease with which the enzymes are capable of degrading a large number of filiform proteins which bind the various vasal endothelid cells, allowing the elements of the blood to escape from the vessels. Although their molecular weights differ greatly, the hemorrhagines maintain however some fixed characteristics on the catalytic site, in the way that Zinc bonds with certain amino acids of the proteic chain, and in the way in which they attack the proteins of the basal membrane of blood vessels. They also seem to have in common the mechanism which ensures the protection of the snake's organism from the toxic effects of its own metalloproteinases, which seems based on the production of tripeptides capable of functioning as competitive inhibitors, interacting with the active site of the enzyme containing Zinc (Biomed.Biochim.Acta 50, 769–773, 1991).

Now the presence of Zinc in the active site of the enzyme constitutes one of the most interesting aspects of the study of Hemorrhagines. In fact this characteristic is not exclusively theirs, but characterizes a wide number of proteolytic enzymes which perform a series of important and diversified physiological and pathological functions in other animal organisms, evolutively also quite distant from each other. In relation to this a comparative study was carried out to determine possible similarities and differences in structure.

By studying the sequences of residues of the proteic chains and the amino acids involved in Zinc bonding it has been possible to obtain a sort of "family tree" for this family of proteinases (see for example FEBS Letters 312, 110–114, 1992 and Developmental Biology 180, 389–401, 1996): it has thus been seen that the active site of enzymes belonging to living beings quite distant from each other, such as Astatin (extracted from a river crustacean), Seratin (obtained from a microorganism), Matrixines (present in the organism of mammals) and those of Hemorrhage Factors of snake venom, in reality differ only in one of the four amino acids binding Zinc. Thus in spite of the fact that there are strong differences in the rest of the proteic structure, they can be considered to be in some way evolutively correlated. This is particularly interesting when considering the fact that the functions performed by these enzymes are not in any way analogous. In fact it has been ascertained that proteolytic enzymes of snake venom if on one hand are very similar and have thus allowed the definition of a proper new family of proteinases: snake venoms metalloproteinases (see for example Biol.Chem. Hoppe-Seyler 373, 381–385, 1992), on the other hand, they do not show any functional similarity with any other protein of the plant or animal world. In particular an extremely relevant fact is the difference between the functionality of hemmorhagines and those of Human Matrixines, which exercise important effects on cell migration and on the reconstruction of damaged tissues. Moreover, while Matrixines are released in the form of "zimogens" (that is, inactive enzymes which must be made functional through other proteinases intervention), and can be inhibited by particular proteins (TIMP), hemorrhagines are immediately active at the moment of dilution in the blood flow. In spite of such structural and functional differences the Applicant has determined the existence of a close correspondence between the inhibition of snake hemorrhagines and the pharmacological results obtained on animal models in which the patogenous agent is presumed to be a zinc-dependent metalloproteinase produced by the tissues of the mammal. Such correspondence seems the consequence of a structural resemblance existing albeit only in the active site between two different types of metalloproteinases and, based on this, the Applicant has developed a method for the selection of compounds for potential therapeutic use in man (Italian patent application RM95A000557; European patent application EP0758021).

Many mammal zinc-dependent metalloproteinases in fact have been related with pathological situations, some of which have been mentioned above. For example gelatinases seem involved in tumoral metastatization, while collagenases have a pathogenic role in arthritic phenomena.

EP-A-0 401 963 describes phosphonopeptides showing an inhibitory activity in regard to enzymes of the collagenase family and as such the compounds are considered useful in the treatment of arthritic and other diseases.

Certain compounds which inhibit matrixines have begun the phases of clinical development in patients suffering from tumour or arthritis: however they are usually scarcely absorbed when administered orally, and are constituted by hydroxamates, compounds which can present toxicity problems in chronic administration.

Finally, a new family of zinc-dependent metalloproteinases was recently identified, localized on the cell membrane, which possess the same proteic domains of hemorrhagines, and are thus considered their closest relatives (see Developmental Biology 180, 389–401, 1996). These proteinases, called ADAM (A Disintegrin and A Metalloproteinase Domain), are correlated with the functionality of the reproductive apparatus, but are also responsible for releasing TNF-a (Tumor Necrosis Factor alfa) and ACE in the circulation and seem correlated to SNC diseases, including Multiple Sclerosis.

SUMMARY OF THE INVENTION

The aim of the present invention is to supply compounds with pharmacological activity towards human pathologies, which have been securely related with the enzymatic activity of zinc-dependent metalloproteinases.

The strategy followed to solve this problem was to take as starting-points the ascertained resemblance in the structure of the active site existing between Hemorrhagines and other mammal zinc-dependent metalloproteinases, and the mechanism of protection of the snake against the effects of its own venom, based on the production of peptides inhibiting the enzymatic activity of Hemorrhagines themselves.

Based upon these data, the synthesis of new compounds capable of acting as inhibitors of the snake's proteinases was designeded, supposing that, given the structural resemblance in the active site, they could also act as inhibitors of human zinc-dependent metalloproteinases.

Therefore, a first step consisted in designing these compounds on the basis of the three-dimensional characteristics of the active site of a Hemorrhagine resolved on X-ray, Adamalysin II, and of the known data concerning the "natural" inhibitors of such enzyme.

In this way in fact it is possible not only to visualize the relative structure of each single domain of the protein, but also to verify the relationship of domains within the quaternary structure of the protein. It is therefore possible to obtain some structural data which together with the enzymatic data offer a significant contribution to the comprehension of the action-inhibition mechanism of a given protein. It has thus been possible to design and build certain compounds potentially capable of binding the active site and of acting as inhibitors of the protein itself.

As an outcome of this phase it has been possible to arrive at a definition of these "peptido-mimetic" compounds, that is, similar to peptides, but lacking at least one of the bonds that make molecules easily attackable by the proteolytic enzymes, with an important characteristic in the substitution of the residue of the terminal tryptophan with the analogous phosphonate.

The compounds according to the present invention can be represented according to the following general formula:

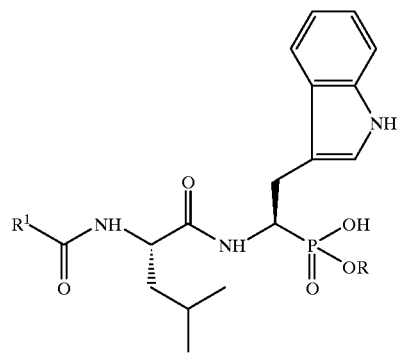

in which R can be H, or $CH_2$—$C_6H_5$, and R' can be a saturated or aromatic ring formed by five or six members, of which one at least is not carbon, but can be selected among nitrogen, oxygen and sulphur. An example is supplied by the following structures:

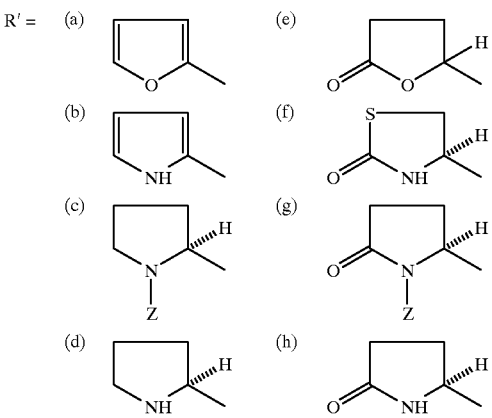

Such compounds were then obtained through two different synthesis schemes, confluent into one another in the final phase.

In Diagram 1, diethylester of (1)-phosphotryptophan (1) obtained by using a modified version of the method described above (Subotkowski, J., Kowalik J., Tyka R., Mastalerz P. *Pol.J.Chem.* 1981, 55, 853–857; Rogers R. S., Stern M. K. *Synlett.* 1992, 708), (i.e., the reduction of 1-hydroxymino-2-(3-indolyl) ethane phosphonate with aluminium amalgam in presence of aqueous ammonia), is reacted with a pseudo-peptide, obtained by acylation of leucin with R'—COOH acid, where R' represents a saturated or aromatic ring, formed by five or six members, of which at least one is not constituted by carbon, but can be selected among nitrogen, oxygen and sulphur. The resulting diethyl esters (3) are thus transformed into the corresponding free phosphonic acids which were isolated, purified and kept as cyclohexylmaine salts (4).

In the specific case of compound 5, said compound was obtained and isolated as an inner salt. This occurs also with other saturated rings of 5 or 6 member containing nitrogen.

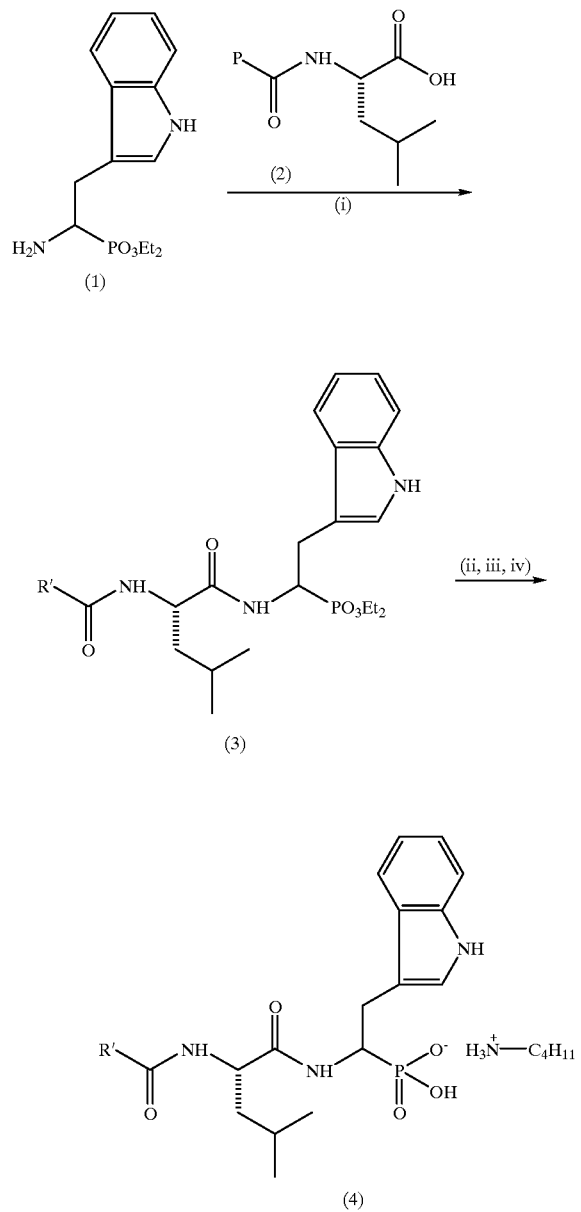

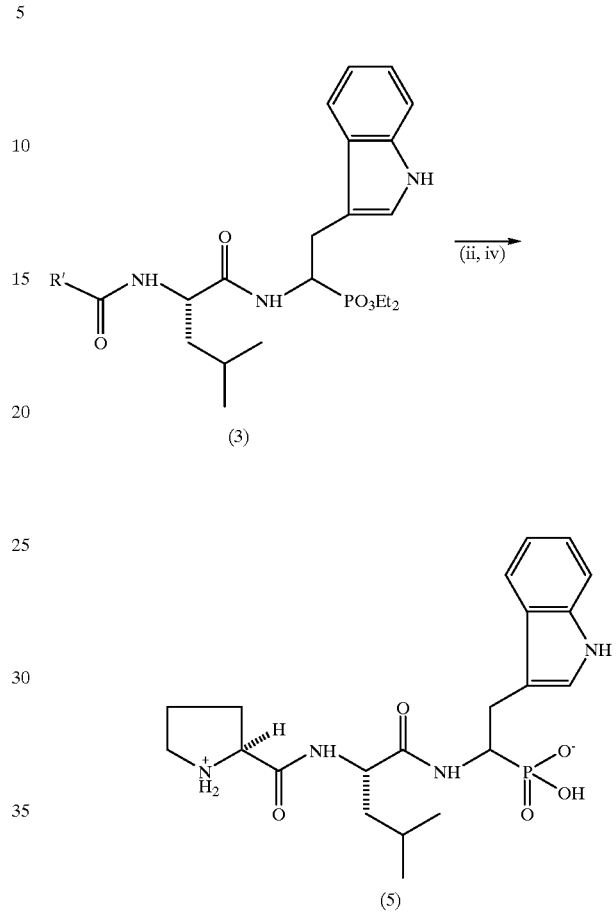

The conditions under which the aforementioned experiments were carried out are indicated by symbols in the diagram and are the following: (i) DCC, 1-HBT, THF, 15 h, 53–73%; (ii) N,O-bistrimethylsilyl-acetamide, Me$_3$SiI, CH$_2$Cl$_2$, 25° C., 2 h; (iii) C$_6$H$_{11}$NH$_2$AcOEt, 40–86%; (iv) 10% Pd/C, EtOH, 25° C., 2 h, 85%.

In Diagram 2 instead indoleacetic acid (6) is converted into benzyl diethyl-ester (8) of phosphotryptophan.

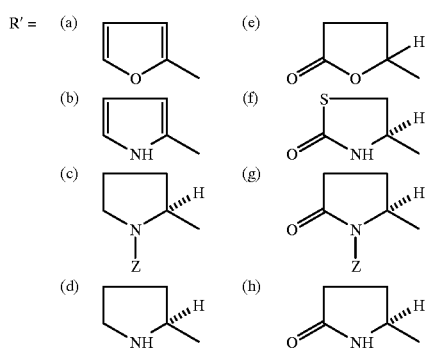

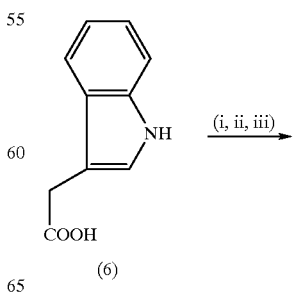

-continued

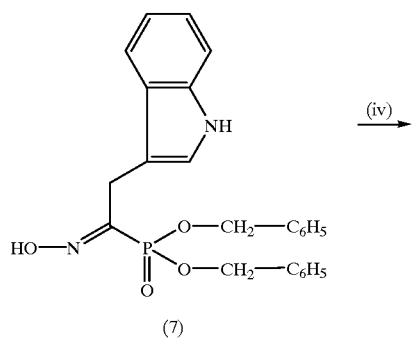

(7)

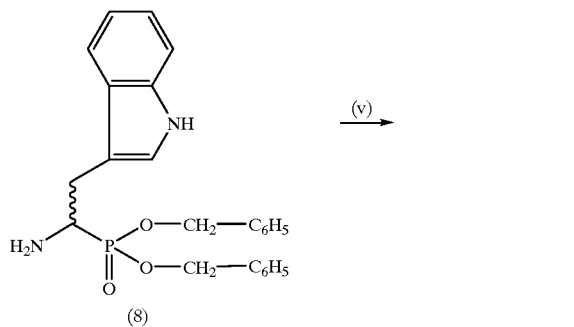

(8)

The compound thus obtained (8) is then reacted with the pseudo-peptides already used in the synthesis scheme described previously.

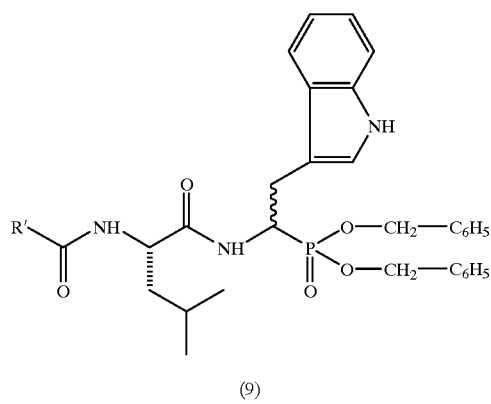

The removal of only one of the two benzyl groups produces monobenzylester (10).

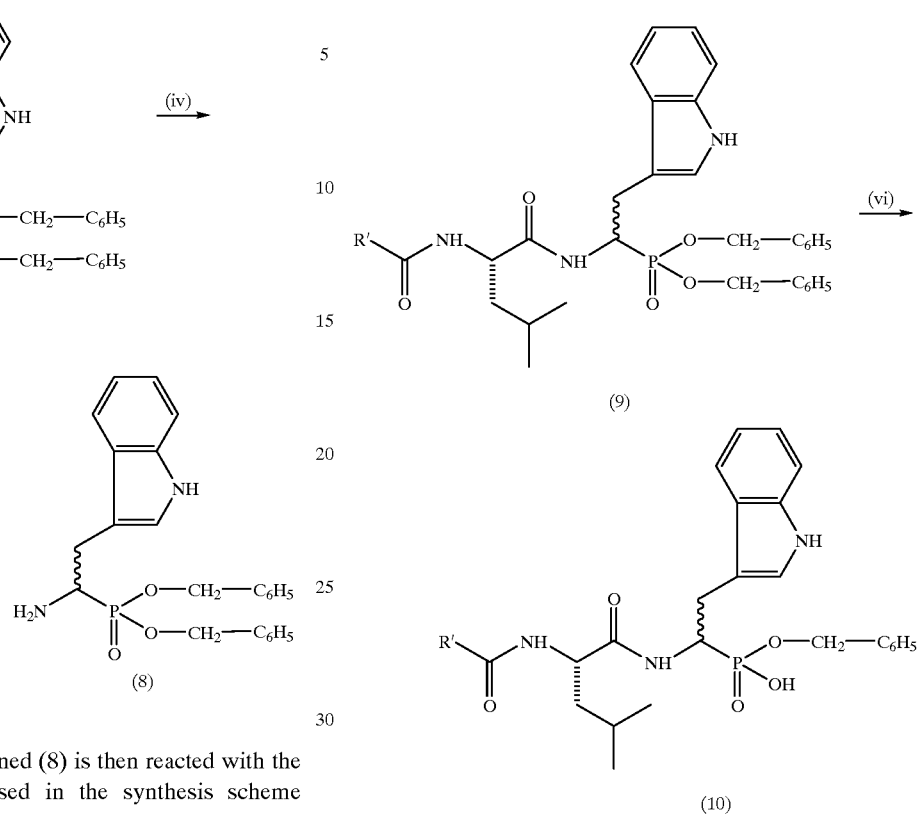

The reaction conditions are here too summarily distinguished by symbols and are listed below: (i) ClCO—COCl, $CH_2Cl_2$, 0.3% DMF, refl, 30 min; (ii) $Me_3Si$-O-P (O—CH$_2$—C$_6$H$_5$)$_2$, $CH_2CL_2$, −18° C., 1 h; (iii) $NH_2OH$ HCL, $C_5H_5N$, EtOH, from −18 to 4° C., 15 h 46%; (iv) AlHg, $NH_4OH$, EtOH, 25° C., 2 h, 68%; (v) R'—CO—Leu—OH, i—Bu—O—CO—Cl, NMM, THF, −20° C., 88%; (vi) AlHg, $NH_4OH$, EtOH, 25° C., 4days, 58%.

STUDY OF PHARMACOLOGICAL ACTIVITY

The therapeutic activity of pseudo-peptides thus obtained was verified applying the method previously devised by the Applicant (Italian Patent application RM95000957) taking into consideration the specific characteristics of the case.

The compounds thus obtained were first subjected to experiments to test their actual capacity of inhibiting enzymatic activity of snake venom metalloproteinases, having been designed on the relative three-dimensional structure of such metalloproteinases, with respect to the capacity of bonding to the enzymes' active site and thus of acting as competitive inhibitors.

This property was verified in particular by inhibition tests in vitro on metalloproteinase Adamalysin II purified from Crotalus Adamanteus venom, a protein of which the three-dimensional configuration is entirely known, which was also selected because among snake metalloproteinases it is the one closest to human metalloproteinase, due to the remarkable homology of the primary aminoacid sequence which it presents with the enzyme which releases TNF-a in man (TACE) in the active site. The results extensively described in example 5 indicate the existence of a good inhibitory capacity in all tested compounds, some of which show also a remarkable power of action (see infra table I). Because of the resemblance between Adamalysin II and TACE, these results are indicative per se also of a possible pharmacological activity of the compounds against TNF-a.

The next step consisted therefore in testing the inhibitory capacity of such compounds also in relation to human metalloproteinases. Reference proteinases were significantly selected for this reason as neutrophile Collagenases and purified Gelatinases A from human cell cultures.

Gelatinase A also know as MMP-2, is in fact an enzyme belonging to the Matrixin family which have been shown to be produced in great quantity in many pathological situations, and believed to be primarily responsible for the migration of tumoral cells from the blood towards tissues affected by metastasis phases.

Likewise also neutrophile Collagenases (denominated MMP8), also belonging to the matrixin family, has been related with a large number of pathological situations. In particular it is considered primarily responsible for the destruction of cartilage which is observed in cases of chronic inflammation. Consequently, it is quite clear that the identification of inhibitors of the activity of both these proteins must be considered a first and important step to elaborate new efficient therapies for these pathologies.

With reference to these considerations, testing has been carried out on neutrophile Collagenases and Gelatinases A themselves for assessing the effective synthesized compounds capacity to bond to the active site of human metalloproteinase, and so to act as competitive inhibitors.

The results extensively described in examples 5 and 6 have shown the existence of a good (albeit varying from compound to compound) inhibitory capacity of such compounds also for these metalloproteinases. Also considering the fact that the two proteinases perform functions which are also performed by other matrixines, the results obtained for both must therefore be considered as indicative also of the potential inhibitory capacity of the pseudo-peptides object of the present invention on other zinc-dependent matrixines implicated as pathogenetic agents, in many pathological situations in man.

These capacities are thus indicative of a potential use of pseudo-peptides as powerful therapeutic agents, whose efficacy and pharmacological usefulness is enhanced by their peculiar chemical characteristics. The modifications of the peptidic structure of these compounds are likely to make them resistant to gastric proteolytic enzymes, and therefore they can be considered suitable for oral administration. Moreover the substitution of the terminal tryptophan residue with the analogous phosphonate remarkably increases the inhibitory activity on enzymes, without introducing risks of systematic toxicity of molecules presently subjected to clinical testing in tumors and arthritis. In fact they are based on hydroxamate compounds which have great power in bonding zinc, but which after prolonged administration can introduce in the organism an accumulation of hydroxylamin, a potentially cancerogenous agent. The compounds object of the present invention instead, being phosphonates, do not present risks of dangerous side-effects, as is demonstrated by drugs of this category which are on the market now.

With reference to all the above, object of the present invention are compounds of general formula:

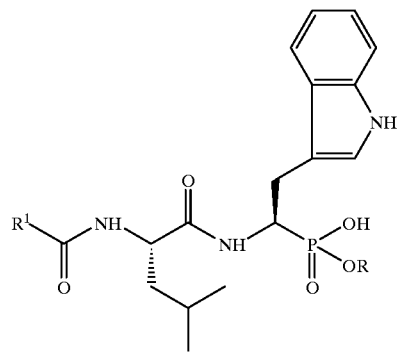

in which R can be H, or $CH_2$—$C_6H_5$, and R' can be a saturated or aromatic ring of five or six members, of which at least one is not carbon, and can be selected among a group including nitrogen, oxygen and sulphur. A particularly preferred case is that in which R' is selected from the group including:

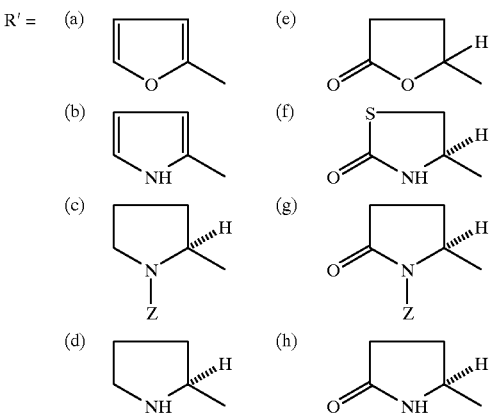

Also object of the present invention is the use of the same as inhibitors of enzymatic activity of at least one of the zinc-dependent metalloproteinases extracted from the venom of snakes belonging to the families of the Crotalidae and of the Viperidae also denominated hemorrhagines (in particular Adamalysin II), and/or at least one of the zinc-dependent metalloproteinases of human origin, of which the active site presents a three-dimensional structure analogous to that of the said snake metalloproteasis (in particular the neutrophile Collagenases, Gelatinases A and the ADAM).

Consequently to all observations reported so far the use of such compounds as pharmaceuticals for the therapeutic treatment of all human pathologies in which the pathogenic mechanism or in which the symptomatology has been demonstrated to include at least one zinc-dependent metalloproteinase, and relative pharmaceutical compounds containing them must also be considered. In particular, reference is made to tumoral growth and metastasization, atherosclerosis, multiple sclerosis, Alzheimer's disease, osteoporosis, hypertension, rheumatoid arthritis, and other inflammatory diseases.

A further object of the present invention is the process for producing the (1)-phosphotryptophan diester as the starting product for the synthesis of the compounds previously described, including as an essential operation the reduction of 1-hydroxymino-2-(3-indolyl) ethane phosphonate by adding an amalgam of aluminum in presence of aqueous ammonia.

A general description of the present invention has been made so far. With the aid of the following example, a more detailed description of specific embodiments will now be given, in order to give a better understanding of the objects, characteristics, advantages and operating methods of the invention. Such examples serve merely to illustrate and do not limit the scope of the present invention.

EXAMPLE 1

Preparation of oxalate of (1)-diethyl-1-amino-2-(3-indolyl) ethane phosphonate (Compound 1)

To a solution of diethyl-1-hydroxymino-2-(3-indolyl) ethane phosphonate (Subotkowski, J., Kowalik J., Tyka R., Mastalerz P. Pol. *J. Chem.* 1981, 55, 853–857) (7.93 g, 25.6 mmols) in EtOH/$H_2O$ 13/1 (38 ml) and acqueous $NH_3$ at 25% (11 ml), under stirring, an amalgam of aluminium (15 g) was added. After 19 hours at room temperature the reaction mixture was filtered on kieselguhr and the solution was concentrated at reduced pressure. The raw product was dissolved in EtOAc (500 ml) and extracted with NaOH 1N (100 ml) and NaCl saturated solution (100 ml). After drying the organic phase on $Na_2SO_4$, the solvent was removed at a reduced pressure. The raw product was dissolved in EtOAc (40 ml) under stirring, and added dropwise with a solution of oxalic acid (2.30 g, 25.6 mmols) in EtOAc (40 ml). The salt formed as a chrystalline hygroscopic solid was recovered by filtration: 9.88 g (100%).

The (1)-diethyl-1-amino-2-(3-indolyl) ethane phosphonate (1) used in the subsequent transformations was obtained by separation from the racemic form by employing D-(+)-dibenzyltartaric acid (Lavielle G., HautHautefaye P, Schaeffer C., Boutin J. A., Cudennec C. A., Pierré A. *J. Med. Chem.* 1991, 34, 1998–2003).

EXAMPLE 2

Preparation of the pseudo-dipeptides

Preparation of N-[(furan-2-yl)carbonyl]-L-leucine (Compound 2a)

To a solution of furan-2-carboxylic acid (2.0 g, 17.8 mmols) and N-methylmorpholine (1.95 ml, 17.8 mmols) in anhydrous THF (10 ml), cooled at −15° C. was added dropwise under stirring an equivalent quantity of isobutylchloroformate (2.33 ml, 17.8 mmols). After 30 minutes a solution of L-leucine methylester hydrochloride (3.23 g, 17.8 mmol) and N-metylmorpholine (1.95 ml, 17.7 mmols in anhydrous THF (15 ml) was slowly added, maintaining the mixture under stirring at −15° C. for two hours. The reaction mixture was diluted with $CH_2Cl_2$ (100 ml) and washed with HCl 1N (30 ml×2), $NaHCO_3$ saturated solution (30 ml×2), and NaCl saturated solution (30 ml). After drying the organic phase on $Na_2SO_4$ and removal of the solvent at a reduced pressure, the raw product was obtained as an oily residue which spontaneously solidified. By grinding the solid substance in petroleum ether, white crystals of either N-[(furan-2-yl) carbonyl]- L-leucine methylester were obtained: 3.32 g (80%); m.p. 88–90° C., [a] $D^{22}$=−23° C. (1, methanol); IR ($CHCl_3$): 3424, 2956, 1741, 1663, 1595, 1517, 1351, 1177 cm$^{-1}$; $^1$H-NMR (CLCl$_3$): d 0.95 and 1.02 [two s, 6, $CH_2CH(CH_3)_2$], 1.45–2.00 [m, 3, $CH_2CH(CH_3)_2$], 3.85 (s, 3, $OCH_3$), 4.73–5.13 (m, 1, aCH), 6.39–7.45 [m, 3, furan aromatics and 6.89 (d, 1, NH, J=8 Hz)]. Calculated for $C_{12}H_{17}NO_4$: C, 60.24; H 7.16; N 5.85. Found C 60.15; H 7.22; N 5.88%.

A solution of N-[(furan-2-yl)carbonyl]-L-leucine methylester (2.73 g, 11.4 mmols) and dioxane/MeOH 7/1 (80 ml) and NaOH 1N (22.8 ml) was kept at room temperature for one night. After concentrating the solvent at reduced pressure the alkali acqueous phase was diluted in $H_2O$ (20 ml), washed with $Et_2O$ (30 ml×2), acidified with HCl 2N and extracted with $CHCl_3$ (70 +30 ml). The organic phases were washed with NaCl saturated solution (30 ml×2), dried on $Na_2SO_4$ and evaporated at reduced pressure. The crystallization of the raw product from $CH_2Cl_3$/petroleum ether was provided the pure product (2a) in white solid form: 2.24 g (90%); m.p. 80–3° C.; [a]$D^{22}$=−10° C. (1, methanol); IR ($CHCl_3$): 3426, 2957, 1721, 1659, 1593, 1419, 1179, 1011 cm$^{-1}$; $^1$H-NMR (MeOD): d 0.75–1.08 [m, 6, $CH_2CH(CH_3)2$], 1.50–1.83 [m, 3, $CH_2CH(CH_3)_2$], 4.32–4.80 (m, 1, aCH), 6.30–7.46 (m, 4, furan protons). Calculated for $C_{11}H_{15}NO_4$: C, 58.66; H, 6.71; N, 6.22. Found C, 58.34; H, 6.33; N, 6.01%.

Preparation of N-[(pyrrol-2-yl)carbonyl]-L-leucine (Compound 2b).

To a solution of pyrrol-2-carboxylic acid (1.11 g, 10 mmols), L-leucine methylester hydrochloride (1.82 g, 10 mmols) and N-methylmorpholine (1.09 ml, 10 mmols) in EtOAc (25 ml), cooled at 0° C., was added under stirring, a solution of DCDI (2.06 g, 10 mmols) and HBT (13 mg, 1 mmols) in EtOAc (5 ml). After standing for one night at room temperature, the N,N'-dicyclohexylurea and the N-methylmorpholine hydrochloride were separated by filtration.

The reaction mixture was then diluted with 100 ml of EtOAc and extracted with HCl 1N (40 +20 ml), $NaHCO_3$ saturated solution (40+20 ml) and NaCl saturated solution (40 ml). After drying of the organic phases reunited on $Na_2SO_4$, the solvent was eliminated at reduced pressure. The crystallization of raw material from sim-dichloroethane/n-hexane gave N-[(pyrrol-2-yl)carbonyl]-L-leucine methylester as a light pink solid: 1.73 g (73%); m.p. 131–2° C.; [a]$D^{22}$=−13° C.(1, methanol); IR ($CHCl_3$): 3450, 2956, 1737, 1642, 1553, 1551, 1179, 1113 cm$^{-1}$; $^1$H-nmr (CLCl$_3$): d 0.88 and 0.95 [two s, 6, $CH_2(CH_3)_2$], 1.47–1.80 [m, 3, $CH_2CH_3)_2$], 3.62 (s, 3, $OCH_3$), 4.50– 4.82 4M, 1, ACH7, 5.97–675 (m, 4, pyrrol aromatics and NH), 9.92 (bs, 1, pyrrol NH). Anal. Calculated for $C_{12}H_{18}N_2O_3$: C, 60.49, H; 7.61; N, 11.78, Found C, 60.72; H, 7.82; N, 11.87%.

A solution of N-[(pyrrol-2-yl)carbonyl]-L-leucine methylester (1.82 g, 7.62 mmols) in dioxane/MeOH 7/1 (80 ml) and NaOH 1N (15.24 ml) was kept at room temperature for one night. After concentrating the solvent at reduced pressure the alkali acqueous phase was diluted in $H_2O$ (15 ml), washed with $Et_2O$ (25 ml×2), acidified with HCl 2N and extracted with $CHCl_3$ (60+20 ml). The organic phases were washed with NaCl saturated solution (20 ml×2), dried on $Na_2SO_4$ and evaporated at reduced pressure. The crystallization of the raw product from sim-dichloroethane provides the pure product (2b) as white crystal: 708 mg (41%); m.p. 78–80° C.; [a]$_D^{22}$=−8° (1, acetonitrile); IR ($CHCl_3$): 3448, 3262, 2957, 1713, 1640, 1553, 1437, 1185, 1042, cm$^{-1}$; $^1$H-NMR ($CDCl_3$): d 0.75–1.05 [m, 6, $CH_2CH(CH_3)_2$], 1.40–1.85 [m, 3, $CH_2CH(CH_3)_2$], 4.07–4.48 (m, 1, aCH), 5.78–6.72 (m, 3, pyrrol aromatics), 7.75 (d, 1, NH, J=4.5 Hz), 8.0 (s, 1, NH of pyrrol), 10.59 (bs, 1, COOH). Calculated, per $C_{11}H_{16}N_2O_3$: C, 58.91; H, 7.19; N, 12.49. Found C, 58.53; H, 7.18; N 12.20%.

Preparation of N-{[(S)-(5-oxo-tetrahydrofuran-2-yl)carbonyl]}-L-leucine (Compound 2e).

To a solution of (S)-(+)-5-oxo-tetrahydrofuran-2-carboxylic acid (1.0 g, 7.68 mmols) and N-methylmorpholine (0.84 ml, 7.68 mmols) in anhydrous/THF anhydrous dioxan 2/1 (15 ml), cooled at −15° C. was added dropwise, under stirring, the equivalent quantity of isobutylchloroformate (1.04 ml, 7.68 mmols). After 30 minutes a solution of L-leucine tertbutylester (1.44 g, 7.68 mmols) and anhydrous THF (5 ml) was slowly added, maintaining the mixture under stirring at −15° C. for two hours. The reaction mixtures was diluted with $CH_2Cl_2$ (70 ml) and washed with NaCl saturated solution (20 ml) $KHSO_4$ 1M (20+10 ml), $NaHCO_3$ saturated solution (20+10 ml) and NaCl saturated solution (20 ml). The organic phase was dried on $Na_2SO_4$ and concentrated at reduced pressure. The raw product was purified through chromatography on silica gel ($CH_2Cl_2$/i-PrOH 98/2). By grinding in n-hexane the solid raw residue, the N-{[(S)-(5-Oxo-tetrahydrofuran-2-yl)carbonyl]}-L-leucine tertbutyl-ester was obtained as white crystals: 920 mg (40%); m.p. 79–81° C.; $[a]_D^{22}$=−25° (1, methanol); IR ($CHCl_3$): 3415, 2934, 1788, 1727, 1677, 1517, 1369, 1149 $cm^{-1}$; $^1$H-NMR ($CDCl_3$): d 0.87 and 0.97 [two s, 6, $CH_2CH(CH_3)_2$], 1.18–1.62 [m, 3, $CH_2CH(CH_3)_2$ and 1.40 (s, 9, $C(CH_3)_3$], 2.15–2.80 (m, 4, ring $CH_2CH_2$), 4.25–4.55 (m, 1, ring CH), 4.62–4.88 (m, 1, aCH), 6.56 (d, 1, NH, J=8 Hz). Calculated for $C_{15}H_{25}NO_5$: C, 60.18; H, 8.42; N, 4.68. Found C, 60.12; H, 8.61; N, 4.65%.

To a solution of N-{[(S)-(5-Oxo-tetrahydrofuran-2-yl)carbonyl]}-L-leucine tertbutylester (800 mg, 2.67 mmols) in $CH_2Cl_2$ (3.0 ml) cooled at 0° C., was added freshly distilled anhydrous trifluoroacetic acid (0.5 ml). After a night at room temperature the solvent was evaporated at reduced pressure and the residue was dissolved in $Et_2O$. By adding n-hexane the compound (2e) separated as a brown oil and was dried and decanted in high vacuum; 650 mg (100%); $[a]_D^{22}$=−7° (1, methanol); IR ($CHCl_3$): 3413, 3036, 2957, 1787, 1725, 1678, 1526, 1172, 1191 $cm^{-1}$; $^1$H-NMR ($CDCl_3$): d 0.87 and 0.93 [two s, 6, $CH_2CH(CH_3)_2$], 1.37–1.83 [m, 3, $CH_2CH(CH_3)_2$], 2.06–2.73 (m, 4, ring $CH_2CH_2$), 4.30–4.63 (m, 1, ring CH), 4.67–4.92 (m, 1, aCH), 6.92 (d, 1, NH, J=8 Hz), 8.15 (s, 1, COOH). Calculated for $C_{17}H_{30}N_2O_5 \cdot ½ H_2O$ (cyclohexylamine salt): C, 56.66; H, 8.89; N, 7.77. Found C, 57.00; H, 9.12; N 8.13%.

Preparation of N-{[(R)-(2-oxo-thiazolidine-4-yl)carbonyl]}-L-leucine (Compound 2f).

To a solution of (R)-(−)-2-oxo-thiazolidine-4-carboxylic acid (1.49 g, 10.2 mmols), L-Leucine methylester hydrochloride (1.85 g, 10.2 mmols) and N-methylmorpholinee (1.12 ml, 10.2 mmols) in anhydrous THF (15 ml), cooled at 0° C., was added, under stirring, a solution of DCDI (2.10 g, 10.2 mmols) and HBT (13 mg, 1 mmols) in anhydrous THF (8 ml). After standing one night at room temperature, the N,N'-dicyclohexylures and the hydrochloride of N-methylmorpholines were separated by filtration and the filtered substance was concentrated at reduced pressure. The product was purified by dilution of the raw reside with $CHCl_3$ (50 ml) and extraction with saturated $NaHCO_3$ solution (20 ml×2) and saturated NaCl solution (30 ml). Drying of the organic phase reunited on $Na_2SO_4$ and the removal of the solvent at reduced pressure provided the N-{[(R)-(2-Oxo-thiazolidine-4-yl)carbonyl]}-L-leucine methylester which was crystallized with EtOAc: 1.94 g (69%); m.p. 125–6° C.; $[a]_D^{22}$=−79° (1, methanol); IR ($CHCl_3$): 3412, 2956, 1734, 1678, 1515, 1434, 1338, 1158 $cm^{-1}$; $^1$H-NMR ($CHCl_3$): d 0.90 and 0.95 [two s, 6, $CH_2CH(CH_3)_2$], 1.42–74 [m, 3, $CH_2CH(CH_3)_2$], 3.37–3.85 [m, 2, $CH_2S$ and 3.63 (s, 3, $OCH_3$)], 4.18–4.69 (two m, 2, aCH and ring CH), 7.16 (d, 1, NH, J=8 Hz). Calculated for $C_{11}H_{17}N_2O_4S$: C, 48.34; H, 6.27; N, 10.25. Found C, 48.29; H, 6.80; N, 10.22%.

A solution of N-{[(R)-(2-Oxo-thiazolidine-4-yl)carbonyl]}-L-leucine methylester (2.08 g, 7.58 mmols) in dioxane/MeOH 7/1 (90 ml) and NaOH 1N (23 ml) was kept at room temperature of r6 hours. After concentrating the solvent in acqueous alkaline phase it was diluted with $H_2O$ (20 ml), washed with $Et_2O$ (30 ml×2), acidified with HCl 2N and extracted with EtOAc (78+30 ml). The organic phases were washed with saturated NaCl solution (20 ml×2), dried on $Na_2SO_4$ and evaporated at reduced pressure. By crystallization of EtOAc the pure product was obtained (2f) as white crystals: 643 mg (32%); m.p. 90–3° C.; $[a]_D^{22}$=−69° (1, methanol); IR ($CHCl_3$): 3297, 1672, 1446, 1405, 1369, 1157 $cm^{-1}$; $^1$H-NMR (DMSO-d6): d 0.70–0.97 [m, 6, $CH_2CH(CH_3)_2$], 1.35–1.76 [m, 3, $CH_2CH(CH_3)_2$], 3.09–3.68 (m, 2, $CH_2S$), 3.95–4.30 (m, 2, aCH and ring CH), 7.85– 8.07 (m, 2, 2NH), Calculated per $C_{10}H_{16}N_2O_4S$: C, 46.14; H, 6.20; N, 10.76. Found C, 45.75; H, 6.16; N, 10.36%.

Preparation of N-benzyloxycarbonyl-L-pyroglutamyl-L-leucine (Compound 2g).

To a solution of N-benzyloxycarbonyl-L-pyroglutamic acid (1.6 g, 6.0 mmols) and N-methylmorpholine (0.66 ml, 6.0 mmols) in anhydrous THF (10 ml), cooled at −15° C. was added dropwise under stirring an equivalent quantity of isobutylchloroformate (0.82 ml, 6.0 mmols). After 10 minutes a solution of L-leucine tertbutylester hydrochloride (1.34 g, 6.0 mmols) and N-methylmorpholinee (0.66 ml, 6.0 mmols) in anhydrous THF (9 ml) was slowly added maintaining the temperature at −15° C. for 2 hours. The reaction mixture was diluted with EtOAc (70 ml) and washed with saturated NaCl solution (20 ml), $KHSO_4$ 1M (20+10 ml), saturated $NaHCO_3$ solution (20+10 ml) and saturated NaCl solution (20 ml). The organic phase was dried on $Na_2SO_4$ and the solvent was removed at reduced pressure. The crystallization of raw material from EtOAc/n-hexane gave N-benzyloxycarbonyl-L-pyroglutamyl-L-leucine tertbutylester as white crystals: 2.0 g (77%); m.p. 130–1° C.; $[a]_D^{22}$=−70° (1, methanol); IR ($CHCl_3$); 3420, 2958, 1794, 1723, 1514, 1303, 1152 $cm^{-1}$; $^1$H-NMR ($CDCl_3$): d 0.8–0.91 [m, 6, $CH_2CH(CH_3)_2$], 1.20–1.67 [m, 3, $CH_2CH(CH_3)_2$ and 1.43 (s, 9, $OC(CH_3)_3$], 2.00–2.93 (m, 4, $CH_2CH_2$ of pGlu), 4.27–4.61 (m, 2, 2 aCH), 5.22 (s, 2, $CH_2$ benzylico), 6.24 (d, 1, NH, J=8 Hz), 7.28 (s, 5, benzylic aromatics). Calculated for $C_{23}H_{32}N_2O_6$: C, 63.87; H, 7.46; N, 6.48; Found C, 64.20; H, 7.60; N, 6.48%.

A solution of N-benzyloxycarbonyl-L-pyroglutamyl-L-leucine tertbutylester (1.0 g, 2.3 mmols) in freshly distilled anhydrous trifluoroacetic acid (3 ml), was kept at 0° C. for 30 minutes and for 4 hours at room temperature. Excess trifluoroacetic acid was removed at reduced pressure and the arc product was dried under high vacuum for 2 hours. The crystallization of EtOAc/$Et_2O$ gave a pure product (2 g) as a white solid: 721 mg (83%); m.p. 164–5° C.; $[a]_D^{22}$=−45° (1, methanol); IR (KBr), 3336, 3094, 1767, 1654, 1554, 1305, 1288, 1267, 1197, 1153 $cm^{-1}$; $^1$H-NMR (MeOD): d 0.75–1.02 [m, 6, $CH_2CH(CH_3)_2$], 1.42–1.77 [m, 3, $CH_2CH(CH_3)_2$], 2.00–2.73 (m, 4, $CH_2CH_2$ of pGlu), 4.29–4.77 (two s, 2, 2 aCH), 5.23 (d, 2, benzylic $CH_2$, J=3 Hz), 7.36 (s, 5, aromatics). Calculated per $C_{19}H_{24}N_2O_6$: C, 60.63; H, 6.43; N, 7.44. Found C, 60.38; H, 6.09; N, 7.27%.

EXAMPLE 3

Acylation of (1)-phosphotryptophan diethylester and preparation of cyclohexylamine salts of the acyl-L-leucyl derivatives of d(1)-phosphotryptophan. General procedure.

A) To a solution of the required L-leucyl derivative (1 mmols) and of (1)-phosphotryptophan diethylester (1 mmols) in anhydrous THF (5 ml) cooled at 0° C., under stirring, is added a solution of DCDI (206 mg, 1 mmols) and HBT (14 mg, 0.1 mmols) in anhydrous THF (5 ml). After resting one night at room temperature the N,N'-dicyclohexylurea is separated by filtration and is concentrated at reduced pressure. The solution of the residue in 30 ml di EtOAc, is extracted with saturated $NaHCO_3$ solution (20×2 ml) and saturated NaCl solution (15 ml). After drying is removed at reduced pressure.

B) To a solution of acyl-L-leucyl-(1)-phosphotryptophan diethylester (1 mmols) in anhydrous $CH_2Cl_2$ (10 ml), under stirring in nitrogen atmosphere, an excess of N,O-bis (trimethylsilyl)acetamide (BSA) (11 mmole, 2.69 ml) is added. After 1 hour at room temperature the reaction mixture is cooled at –20° C. and an excess of iodotrimethylsilane (8 mmols, 1.1 ml) is added dropwise. At the end of the addition of the reactive substance the solution is brought to 0° C. within an hour and maintained at room temperature for other 2 hours. The dark oily residue, obtained through concentration at low pressure of the reaction mixture, is treated with $CH_3CN/H_2O$ 7.3 (3 ml) for 1 hour. After removing the solvent at reduced pressure the oily residue is dissolved in EtOAc (40 ml) and washed with $Na_2SO_4$ 1.5% in HCl 1N (10 ml×2) and saturated NaCl solution (10 ml). The organic phase is dried on $Na_2SO_4$ and the solvent is removed at reduced pressure. The raw product, dissolved in EtOAc (4.5 ml), is treated dropwise with a solution of cyclohexylamine (1 mmole) in EtOAc (4.5 ml). Having taken the form of a solid hygroscopic crystal the salt is recovered by filtration.

Preparation of N-[(furan-2-yl)carbonyl]-L-leucyl-(1)-phosphotryptophan salt of cycloexyl-amine (Compound 4a).

N-[(Furan-2-yl)carbonyl]-L-leucyne (2a, 536 mg, 2.38 mmols) and (1)-phosphotryptophan diethylester (705 mg, 2.38 mmols) were reacted according to procedure A. The raw product was purified by chromatography on silica gel ($CHCl_3$/i-PrOH 98/2), obtaining the N-[(furan-2-yl) carbonyl]-L-leucyne-(1)-phosphotryptophan diethylester (3a) in the form of foam: 733 mg (62%); $[a]_D^{22}$=–55° (1, methanol); IR ($CHCl_3$): 3478, 3418, 1660, 1474, 1244, 1026 $cm^{-1}$; $^1$H-NMR ($CDCl_3$): d 0.88 [(2d, 6, $CH_2CH(CH_3)_2$, J=6.1 Hz], 1.20–1.40 [m, 8, $CH_3CH_2O$ and 2 di $CH_2CN$ $(CH_3)_2$], 1.60 [m, 1, 1 di $CH_2CH(CH_3)_2$], 3.11 and 3.35 (two m, 2, $bCH_2$ $Trp^P$), 4.12 (m, 4, $2CH_3CH_2O$), 4.64 (m, 1, aCH Leu), 4.77 (m, 1, aCH $Trp^P$), 6.56 (d, 1, NH Leu, J=8.8Hz), 6.90 (d, 1, NH-CO $Trp^P$), 6.48–7.61 (m, 8, 5 aromatics of indole and 3 aromatics of furan), 8.10 (s, 1, NH of the indole). Calculated for $C_{25}H_{34}N_3O_6P.\raisebox{0.5ex}{$\scriptstyle 2$}\!/\!\raisebox{-0.5ex}{$\scriptstyle 3$}\ H_2O$: C, 58.85; H, 6.98; N, 8.24. Found C, 58.40; H, 6.66; N, 7.85%.

N-[(Furan-2-yl)carbonyl]-L-leucyne-(1)-phosphotryptophan diethylester (3a, 150 mg, 0.298 mmols), BSA (0.80 ml, 3.27 mmols) and TMSI (0.32 ml, 2.38 mmols) were reacted according to procedure B. By means of treatment with cyclohexylamine (29 mg, 0.298 mmols) the pure product is obtained (4a) as a hygroscopic solid: 128 mg (79%); $[a]_D^{22}$=–67° (1, methanol); IR (KBr) 3291, 2937, 1631, 1528 $cm^{-1}$; $^1$H-NMR (DMSO-$d_6$): d 0.80 [m, 6, $CH_2CH(CH_3)_2$], 0.95–2.01 [m, 13, $(CH_2)_5$ cyclohexylamine and $CH_2CH(CH_3)_2$], 2.83 (m, 2, CHN cyclohexylamine and 1H of $bCH_2$ $Trp^P$), 3.29 (m, 1, 1H of $bCH_2$ $Trp^P$), 4.13 (m, 1, aCH $Trp^P$), 4.47 (m, 1, aCH Leu) 6.91–7.88 [(m, 9, aromatics of indole, of furan and 7.74 (d, 1, J=9.3 Hz, NH of $Trp^P$)], 8.48 (d, 1, J=8.9 Hz, NH Leu), 10.64 (s, 1, NH of indole). Calculated $C_{27}H_{39}N_4O_6P.\!^1\!/\!_2\ H_2O$ (cyclohexylamine salt): C, 58.37; H, 7.26; N, 10.08. Found C, 58.11; H, 6.99; N, 9.81%.

Preparation of N-[(pyrrol-2-yl)carbonyl]-L-leucyl-(1)-phosphotryptophan (compound 4b).

N-[(Pyrrol-2-yl)carbonyl]-L-leucine (2b, 303 mg, 1.35 mmols) and (1)-phosphotryptophan diethyl ester (400 mg, 1.35 mmols) were reacted according to procedure A. The raw product was purified by chromatography on silica gel ($CHCl_3$/i-PrOH 99/1). Through subsequent grinding in anhydrous $Et_2O$ of the solid residue the N-[(Pyrrol-2-yl) carbonyl)-L-leucyl-(1)-phosphotryptophan (3b) was obtained as white crystals: 415 mg (61%); m.p. 172–4° C.; $[a]_D^{22}$=–68° (1, methanol); IR ($CHCl_3$) 3278, 2957, 1632, 1553, 1510, 1332, 1199 $cm^{-1}$; $^1$H-NMR ($CDCl_3$): d 0.80 and 0,87 [two s, 6, $CH_2CH(CH_3)_2$], 1.13–1.83 [m, 8, $2CH_3CH_2O$ and two $CH_2CH(CH_3)_2$], 2.59 and 3.27 (two, m, 2, $bCH_2$ $Trp^P$), 3.79–4.26 (m, 4, $2CH_3CH_2O$), 4.40–5.23 (two m, 2, 2 aCH), 5.83–6.41 (m, 4, pyrrol aromatics and 1 NH), 6.55–7.55 (m, 5, indole aromatics), 8.44 and 8.54 (two s, 2, NH of pyrrol and NH of indole). Calculated for $C_{25}H_{35}N_4O_5P$: C, 59.75; H, 7.02; N, 11.15. Found C, 59.47; H, 6.93; N, 10.77%.

N-[(Pyrrol-2-yl)carbonyl]-L-leucyl-(1)-phosphotryptophan diethylester (3b, 361 mg, 0.72 mmols), BSA (1.93 ml, 7.92 mmols) and TMSI (0.78 ml, 5.76 mmols) were reacted according to procedure B. Through treatment with cyclohexylamine (71.4 mg, 0.72 mmols) the pure product is obtained (4b) as a hygroscopic solid: 339 mg (86%); $[a]_D^{22}$=–74° (1, methanol); IR (KBr) 3277, 2937, 1645, 1524, 1140 1047 $CM^{-1}$; $^1$H-NMR (DMSO-$d_6$): d 0.80 [m, 6, $CH_2CH(CH_3)_2$], 0.96–2.00 (m, 13, $(CH_2)_5$ cyclohexylamine and $CH_2CH(CH_3)_2$], 2.86 (m, 2, CHN cyclohexylamine and 1H of $bCH_2$ $Trp^P$), 3.30 (m, 1, 1H of $bCH_2$ $Trp^P$), 4.17 (m, 1, aCH $Trp^P$), 4.51 (m, 1, aCH Leu) 6.07 (apparent s, 1, CH of pyrrol), 6.75–7.60 [(m, 7, indole aromatics and of pyrrol), 7.72 (d, 1, J=8.0 Hz, NH of $Trp^P$)], 8.37 (d, 1, J=7.7 Hz, NH Leu), 10.67 (s, 1, NH of indole), 12.01 (s, 1, NH of pyrrol). Calculated for $C_{27}H_{40}N_5O_5P.7/2\ H_2O$ (cyclohexylamine salt): C, 53.29; H, 7.72; N, 11.51. Found C, 53.37; H, 7.32; N, 11.41%.

L-Prolyl-L-leucyl-(1)-phosphotrylptophan (Compound 5).

N-Benzyloxycarbonyl-L-propyl-L-leucine (Cash W, D. J. Org. Chem., 1951, 26, 2136), (2c, 490 mg, 1.35 mmols) and (1)-phosphotryptophan diethylester (400 mg, 1.35 mmols) were reacted according to procedure A. The crystallization of the raw material from anhydrous $Et_2O$ provided the N-benzyloxycarbonyl-L-pyrolyl-L-eucyl-(1)-phosphtryptophan diethylester (3c) as a crystal hydroscopic solid: 570 mg (66%); $[a]_D^{22}$=–72° (1, methanol); IR ($CHCl_3$): 3477, 2991, 1687, 1500, 1357, 1217, 1052 $cm^{-1}$; $^1$H-NMR ($CDCl_3$): d 0.78 and 0.82 [two s, 6, $CH_2CH(CH_3)_2$], 1.10–1.39 [m, 9, $2CH_3CH_2O$ and $CH_2CH(CH_3)_2$], 1.42–2.05 (m, 4, b,g $CH_2$ of Pro), 2.81–3.50 (m, 4, $CH_2N$ of Pro and $bCH_2$ of $Trp^P$), 3.80–4.48 (m, 7, $2CH_3CH_2O$ and 3 aCH), 4.98 (s, 2, benzylic $CH_2$), 6.34–7.50 [m, 5, indole aromatic and 7.10 (5, s, benzyl aromatics)], 8.48 (s, 1, NH of indole). Calculated $C_{33}H_{45}N_4O_7P\cdot\frac{2}{3}$ $H_2O$; C, 60.79; H, 7.06; N, 8.59. Found C, 60.47; H, 6.90; N, 8.55%.

N-Benzyloxycarbonyl-L-propyl-L-leucyl-(1)-phosphotryptophan diethylester (3c, 550 mg, 0.86 mmols), BSA (2.3 ml, 9.46 mmols) and TMSA (0.93 ml, 6.88 moles) were reacted according to procedure B. After treatment with $CH_3CN/H_2O$ and removal of solvent at reduced pressure, the solid residue was washed with EtOAc and purified with HPLC (Waters ODS DeltaPack 19×30 mm column; eluent $H_2O/CH_3CN$ 70:30; flux 8 ml/minute; retention time: 10.34 min), obtaining 200 mg of pure product (5) in the form of a crystal hydroscopic solid (40%) $[a]_D^{22}=-97°$ (1, NaOH 1N); IR (KBr) 3337, 3262, 2959, 1642, 1135 1071 cm$^{-1}$1 Calculated for $C_{21}H_{31}N_4O_5P\cdot2$ $H_2O$: C, 51.80; H, 7.19; N 11.51. Found C, 51.70; H, 6.96; N, 10.88%.

Preparation of N-{[(S)-(5-oxo-tetrahydrofuran-2-il) carbonyl]}-L-leucyl-(1)-phospho-tryptophan cyclohexylamine salt (Compound 4a)

N-{[(S)-(5-Oxo-tetrahydrofuran-2-yl)carbonyl]}-L-leucine (328 mg, 1.35 mmols) and (1)-phosphotryptophan diethylester (400 mg, 1.35 mmols) were reacted according to procedure A. The purification of the raw material through chromatography on silica gel ($CHCl_3/i$-PrOH 95/5) and crystallization from $Et_2O$ petroleum ether provided the N-{[(S)-(5-oxo-tetrahydrofuran-2-yl)carbonyl]}-L-leucyl-(1)-phosphotryptophan diethylester (3e) in hydroscopic solid form: 474 mg (68%); $[a]_D^{22}=-48°$ (1, methanol); IR ($CHCl_3$): 3476, 2992, 1788, 1676, 1517, 1246, 1052 cm$^{-1}$; $^1$H-NMR ($CDCl_3$): d 0.77 and 0.85 [two s, 6, $CH_2CH(CH_3)_2$], 1.10–1.60 [m, 9, $2CH_3CH_2O$ and $CH_2CH(CH_3)_2$], 2.04–2.48 (m, 4, $CH_2CH_2$ of the tetrahydrofuran ring), 3.08–3.43 (m, 2, b$CH_2$ of Trp$^P$), 3.98–5.00 (m, 7, 2 of $CH_3CH_2O$, 2 aCH and CH of the tetrahydrofuran ring), 6.76 (d, 1, NH, J=9.8 Hz), 6.95–7.75 (m, 5, indole aromatics), 8.88 (s, 1, NH of indole). Calculated for $C_{25}H_{36}N_3O_7P\cdot2/3$ $H_2O$: C, 56.28; H, 7.05; N, 7.88. Found C, 55.92; H, 6.83; N, 7.78%.

N-{[(S)-(5-oxo-tetrahydrofuran-2-yl)carbonyl]}-L-leucyl-(1)-phosphotryptophan diethylester (3e, 207 mg, 0.40 mmols), BSA (1.10 ml, 4.36 mmols) and TMSI (0.43 ml, 3.2 mmols) were reacted according to procedure B. Through treatment with cyclohexylamine (34 mg, 0.40 mmols) pure product is obtained (4e) as a hydroscopic solid: 157 mg (82%); $[a]_D^{22}=-63°$ (1, methanol); IR (KBr) 3280, 2934, 1777, 1641, 1552, 1177, 1048 cm$^{-1}$; $^1$H-NMR (DMSO-d$_6$); d 0.77 [m, 6, $CH_2CH(CH_3)_2$], 0.95–2.50 (m, 17, $(CH_2)_5$ della cyclohexylamine, $CH_2CH(CH_3)_2$ and $CH_2CH_2$ of the tetrahydrofuran ring), 2.87 (bs, 2, CHN cyclohexylamine and 1H of b$CH_2$ Trp$^P$), 3.24 (bs, 1, 1H of b$CH_2$ Trp$^P$), 4.27 (bs, 2, aCH Trp$^P$ and aCH Leu), 4.96 (bs, 1, CH of the tetrahydrofuran ring), 6.79–7.60 (m, 5, indole aromatics), 7.77 (bs, 1, NH Trp$^P$), 8.91 (bs, 1, NH Leu), 10.55–10.78 (m, 2, NH of indole and NHCHO). Calculated for $C_{27}H_{45}N_4O_9P\cdot2$ $H_2O$ (cyclohexylamine salt): C, 54.17; H, 7.24; N, 9.36. Found C, 54.22; H, 7.57; N, 9.03%.

Preparation of the N-{[(R)-(2-oxo-thiazolidin-4-yl) carbonyl]}-L-leucyl-(1)-phosphotryptophan cyclohexylamine salt (Compound 4f)

N-{[(R)-(2-Oxo-thiazolidin-4-yl)carbonyl]-L-leucine (2f, 353 mg, 1.35 mmols) and (1)-phosphotryptophan diethylester (400 mg, 1.35 mmols) were reacted according to procedure A. The purification of the raw product through chromatography on silica gel ($CHCl_3/i$-PrOH 95/5) and crystallization from $CHl_3/Et_2O$ gave N-{[(R)-(2-oxo-thiazolidine-4-yl)carbonyl]}-L-leucyl-(1)-phosphotryptophan diethylester (3f) as a hydroscopic solid: 572 mg (73%); $[a]_D^{22}=-89°$ (1, methanol); IR ($CHCl_3$) 3333, 2958, 1678, 1513, 1339, 1260, 1026 cm$^{-1}$; $^1$H-NMR ($CDCl_3$): d 0.69–0.92 [m, 6, $CH_2CH(CH_3)_2$], 1.08–1.65 [m, 9, $2CH_3CH_2O$ and $CH_2CH(CH_3)_2$], 2.92–3.47 (m, 4, $CH_2S$ and b$CH_2$ Trp$^P$), 3.63–4.90 (m, 7, $2CH_3CH_2O$ and 3 aCH), 6.73–7.43 (m, 5, indole aromatics), 8.63 (s, 1, NH of indole). Calculated for $C_{24}H_{35}N_4C_6PS\cdot\frac{1}{2}$ $H_2O$. C, 52.64; H, 6.63; N, 10.23. Found C, 52.86; H, 6.45; N, 10.03%.

N-{[(R)-(2-oxo-thiazolidin-4-yl)carbonyl]}-L-leucyl-(1)-phosphotryptophan diethylester (3f, 404 mg, 0.75 mmols), BSA (2.0 ml, 8.25 mmols) and TMSI (0.82 ml, 6.0 mmols) were reacted according to procedure B. Through treatment with cyclohexylamine (74 mg, 0.75 mmols) pure produce is obtained (4f) as a hydroscopic solid; 312 mg (71%); $[a]_D^{22}=-70°$ (1, methanol); IR (KBr) 3285, 2936, 1641, 1532, 1141, 1047 cm$^{-1}$; $^1$H-NMR (DMSO-d$_6$): d 0.75 [m, 6, $CH_2CH(CH_3)_2$], 1.00–2.00 [m, 13, $(CH_2)_5$ of cyclohexylamine and $CH_2CH(CH_3)_2$], 2.92 (m, 2, CHN of cyclohexylamine and 1H of b$CH_2$ Trp$^P$), 3.15–3.68 (m, 3, 1H of b$CH_2$ Trp$^P$ and $CH_2S$), 4.05–4.40 (m, 3, aCH Trp$^P$ and aCH Leu superimposed over $CHCH_2S$), 6.85–7.68 (m, 5, indole aromatics), 8.05 (d, 1, J=8.6 Hz, NH of Trp$^P$), 8.78 (d, 1, J=8.6 Hz, NH Leu), 9.00 (bs, 1, N$\underline{H}$CH$_2$S), 10.65 (s, 1, NH of indole). The assigning of the NH groups are interchangeable. Calculated for $C_{26}H_{40}N_5O_6P\cdot1$ $H_2O$ (cyclohexylamine salt): C, 52.02; H, 7.00; N, 11.67. Found C, 52.29; H, 7.07; N, 11.38%.

Preparation of N-Benzyloxyicarbonyl-L-Pyroglutamyl-L-leucyl-(1)-phosphotryptophan cyclohexylamine salt Compoundo 4g)

N-Benzyloxycarbonyl-L-pyroglutamyl-L-leucine (2g, 507 mg, 1.35 mmols) and (1)-phosphotryptophan diethylester (400 mg, 1.35 mmols) were reacted according to procedure A. The chromatography on silica gel ($CHCl_3/i$-PrOH 95/5) of the raw product gave N-Benzyloxycarbonyl-L-pyroglutamyl-L-leucyl-(1)-phosphotryptophan diethylester (3g) in the form of foam: 466 mg (53%); [a] D$^{22}$=−73° (1, methanol); IR (KBr) 3287, 2957, 1787, 1654, 1552, 1232, 1028 cm$^{-1}$; $^1$H-NMR (MeOD): d 0.74–1.00 [m, 6, $CH_2CH(CH_3)_2$], 1.13–1.54 [m, 9, $2CH_3CH_2O$ and $CH_2CH(CH_3)_2$], 2.16–2.41 (m, 4, $CH_2CH_2$ of pGlu) 3.21–3.48 (m, 2, b$CH_2$ Trp$^P$), 4.00–4.91 (3m, 7, $2CH_3CH_2O$ and 3 aCH), 5.26 (s, 2, benzylic $CH_2$), 7.00–7.68 [m, 5, indole aromatics and 7.40 (s, 5, benzyl aromatics)]. Calculated for $C_{33}H_{43}N_4O_8P$: C, 60.54; H, 6.62; N, 8.56. Found. C, 60.03; H, 6.63; N, 8.33%.

N-benzyloxycarbonyl-L-pyroglutamyl-L-leucyl-(1)-phosphotryptophan diethylester (3g, 366 mg, 0.56 mmols), BSA (1.5 ml, 6.16 mmols) and TMSI (0.6 ml, 4.48 mmols) were reacted according to procedure B. For treatment with cyclohexylamine (55 mg, 0.56 mmols) pure product is obtained (4g) as an hygroscopic solid: 195 mg (62%); $[a]_D^{22}=-72°$ (1, NaOH 1N); IR (KBr) 3294, 2936, 1786, 1640, 1548, 1305, 1135, 1046 cm$^{-1}$; $^1$H-NMR (DMSO-d$_6$): d 0.70 [m, 6, $CH_2CH(CH_3)_2$], 0.95–2.40 [m, 17, $(CH_2)_5$ cyclohexylamine, $CH_2CH(CH_3)_2$ and $CH_2CH_2$ pGlu], 2.86 (m, 2, CHN of cyclohexylamine and 1 of b$CH_2$ Trp$^P$), 3.25 (m, 1, 1 of b$CH_2$ Trp$^P$), 4.00–4.30 (m, 2, aCH of Trp$^P$ and of the Leu), 4.71 (m, 1, aCH pGlu), 5.09 and 5.15 (A and B of an AB, 2, J=13 Hz, PhC$\underline{H}_2$O), 6.80–7.68 (m, 12, indole aromatics, benzyl aromatics and 2 NH), 8.86 (bs, 1, NH), 10.65 (s, 1, NH of the indole). Calculated. for $C_{35}H_{48}N_5O_8P\cdot1$ $H_2O$ (cyclohexylamine salt): C, 58.67; H, 6.98; N, 9.78. Found C, 58.91; H, 6.97; N, 9.33%.

Preparation of the L-pyroglutamyl-L-leucyl-(1)-phosphotryptophan salt of cyclohexylamine (Compund 4h)

A solution fo N-benzyloxycarbonyl-L-pyroglutamyl-L-luecyl-(1)-phosphotryptophan cyclohexylamine salt (4f) (50 mg), 0.072 mmols) in EtOH/$H_2O$ 5:2 (7 ml) in presence of Pd/C 10% was kept 2 hours in a current of $H_2$. After filtration on paper and removal of the solvent at reduced pressure, the product (4h) was obtained pure in the form of a pink hygroscopic solid: 34 mg (85%). $[a]_D^{22}$=−80° (0.5, MeOH); IR (KBr) 3280, 2936, 1642, 1536, 1149, 1047 cm$^{-1}$; $^1$H-NMR (DMSO-$d_6$): d 0.76 [m, 6, $CH_2CH(CH_3)_2$], 0.95–2.30 [m, 17, $(CH_2)_5$ cyclohexylamine, $CH_2CH(CH_3)_2$ and $CH_2CH_2$ of pGlu], 2.87 (bs, 2, CHN of cyclohexylamine and 1 of $bCH_2$ $Trp^P$), 3.24 (m, 1, 1 of $bCH_2$ $Trp^P$), 3.97–4.30 (m, 3, aCH of $Trp^P$, of Leu and of pGlu), 6.80–7.60 (m, 5, indole aromatics), 7.91 (d, 1, J=8 Hz, NH $Trp^P$), 8.33 (s, 1, NH lactone), 8.50 (d, 1, J=7 Hz, NH Leu), 10.66 (s, 1, NH of indole). Calculated for $C_{27}H_{42}N_5O_6P$.3/2 $H_2O$ (cyclohexylamine salt): C, 54.86; H, 7.62; N, 11.85. Found C, 54.90; H, 7.55; N, 11.50%.

EXAMPLE 4

N[(furan-2-yl)-carbonyl-L-leucyl-phosphotryptophan Monobenzylester (Compound 10)

Preparation of diebenzyl-1-hydroxyimine-2-(3-indolyl)ethanephosphonate (Compound 7)

To a suspension of indoleacetic acid (6, 5 g, 28.5 mmols) in anhydrous $CH_2Cl_2$ (100 ml) and anhydrous DMF (0.3 ml), cooled at 0° C. was added dropwise, under stirring and in atmosphere of oxalyl nitrogen chloride (2.7 ml, 31.4 mmols) within a 30 minute time-span. The reaction mixture was refluxed for 30 minutes. At the end of such period the solvent was evaporated at reduced pressure and the oil residue containing the indoleacetic acid chloride, was dissolved in anhydrous $CH_2Cl_2$ (50 ml). To this solution, cooled at −18° C., was added dropwise, under stirring and in nitrogen atmosphere a solution of dibenzyl trimethylsilyphosphite in anhydrous $CH_2Cl_2$ (100 ml), obtained from dibenzylphosphite (6.33 ml, 28.5 mmols) and trimethylchlorosilane (5 ml, 39.5 mmols) in presence of triethylamine (Afarinkia K., Rees C. W., Cadogan J. I. G.; *Tetrahedron*, 1990, 46, 7175–7196), (4.38 ml, 31.4 mmols). After 1 hour the solvent was removed at reduced pressure and the oily residue dissolved in EtOH (35 ml) and pyridine (3.44 ml, 42.75 mmols). To this solution, cooled at −18° C., was added dropwise and under stirring a solution of hydroxylamine hydrochloride (2.57 g, 37.05 mmols) in MeOH (35 ml). After maintaining the reaction mixture for 12 hours at 4° C. the solvent was removed at reduced pressure and the residue, dissolved in $CHCl_3$ (400 ml), was washed with $H_2O$ (100 ml), saturated $NaHCO_3$ solution (100 ml) and saturated NaCl solution (100 ml). The organic phases were reunited and dried on $Na_2SO_4$ and the solvent was removed at reduced pressure. The purification of raw material through chromatography on silica gel ($CH_2Cl_2$/i-PrOH 95/5) and crystallization through sim-dichloroethane provided the pure product (7), in the form of a solid white crystal: 5.74 g (46%); m.p. 130–1° C.; IR (KBr): 3428, 3187, 1641, 1455, 1425, 1244, 1057 cm$^{-1}$; $^1$H -NMR (DMSO-$d_6$): d 3.77 (bs, 2, $bCH_2$ $Trp^P$), 4.70–4.90 (m, 4, $2CH_2Ph$), 6.80–7.60 (m, 15, aromatics), 10.60 (s, 1, NH of indole), 12.27 and 12.33 (two s, 1, C=N—OH).

Preparation of phosphotryptophan dibenzylester oxalate (Compound 8)

To a solution of dibenzyl 1-hydroxyimine-2-(3-indolyl)ethanphosphonate (7, 2.61 g, 6.01 mmols) in EtOH/$H_2O$ 13/1 (56 ml) and acqueous $NH_3$ at 25% (2.6 ml) was added an aluminum amalgam (3.60 g). After 1 hour the reaction mixture was filtrated on kieselguhr and the filtered substance was concentrated at reduced pressure. The raw product was dissolved in EtOAc (80 ml) and extracted with saturated $NaHCO_3$ solution (20 ml) and saturated NaCl solution (20 ml). After drying the organic phase on $Na_2SO_4$ the solvent was removed at reduced pressure. The raw product dissolved in EtOAc (10 ml), was additioned dropwise with a solution of oxalic acid (600 mg, 6.01 mmols) in EtOAc (10 ml). The pure product (8), separated as a solid hygroscopic crystal, was recovered by filtration: 2.087 g (68%). IR ($CHCl_3$): 3424, 2925, 1702, 1619, 1453, 1229, 1098, 998 cm$^{-1}$; $^1$H-NMR (DMSO-$d_6$): d 2.90–3.43 (m, 2, $bCH_2$ $Trp^P$), 3.60–4.03 (m, 1, aCH $Trp^P$), 4.70–5.13 (m, 4, $2CH_2Ph$), 6.80–7.76 (m, 15, aromatics), 8.07 (bs, 1, NH of indole).

Preparation of N-[(Furan-2-yl)carbonyl]-L-leucyl-(1)-phosphotryptophan dibenzylester (Compound 9)

To a solution of N-[(furan-2yl)carbonyl]-L-leucine (2a, 664 mg, 2.95 mmols), and N-methylmorphonine (0.32 ml, 2.95 mmols) in anhydrous THF (10 ml), cooled at −15° C. was added dropwise, under stirring, an equivalent quantity of isobutylchloroformate (0.39 ml, 2.95 mols). After 30 minutes a solution of dibenzyl-1-amino-2-(3-indolyl) ethanphosphoante was slowly added (8) in anhydrous THF (10 ml) maintaining the mixture under stirring at −15° C. for 2 hours. The reaction mixture was diluted with $CH_2Cl_2$ (50 ) and washed with HCl 1N (10 ml×2), saturated $NaHCO_3$ solution (10 ml×2) and saturated NaCl solution (10 ml). After drying the organic phase on $Na_2SO_4$ and removal of the solvent at reduced pressure, the raw product was purified through chromatography on silica gel ($CH_2Cl_2$/i-PrOH 95/5) obtaining by removing the solvent at reduced pressure the pure product (9) in the form of white foam: 1.63 g (88%); IR ($CHCl_3$) 3477, 3419, 1660, 1594, 1512, 1248, 1011, 998 cm$^{31\ 1}$; $^1$H-NMR ($CDCl_3$): d 0.70 and 0.80 [two s, 6, $CH_2CH(CH_3)_2$], 1.10–1.71 [m, 3, $CH_2CH(CH_3)_2$], 3.10–3.33 (m, 2, $bCH_2$ $Trp^P$), 4.33–4.63 (m, 2, aCH Leu and aCH $Trp^P$), 4.77–4.97 (m, 4, $CH_2Ph$), 6.23–6.67 (two m, 2, amide NH), 6.76–7.47 (m, 18, aromatics), 8.07 (bs, 1, NH of indole).

Preparation on N-[Furan-2-yl)carbonyl]-L-leucyl-(1)-phosphotryptophan monobenzyl-ester (Compound 10)

To a solution of N-[(furan-2-yl)carbonyl]-L-leucyl-(1)-phosphotryptophan dibenzylester (9) (100 mg, 0.159 mmols) in EtOH/$H_2O$ 13/1 (1.5 ml) and acqueous $NH_3$ at 25% (0.07 ml) was added an aluminium amalgam (95 mg). After 4 days, the reaction mixture was filtered on kieselghur and the filtrated. substance was concentrated at reduced pressure. The raw reaction product was dissolved in $CHCl_3$ (10 ml) and extracted with NaOH 0.1N (5 ml×2). The acqueous alkaline phases were acidified with HCl 1N (1.5 ml) and extracted with $CHCl_3$ (10 ml×2). The organic phases were washed with saturated NaCl solution (5 ml), reunited and dried on $Na_2SO_4$. Through evaporation at reduced pressure of the solvent the pure product was obtained (10) in the form of white foam: 49 mg (58%); $[a]_D^{22}$32 −24° (0.5, MeOH); IR ($CHCl_3$) 3477, 3414, 1649, 1595, 1516, 1011 cm$^{-1}$; $^1$H-NMR ($CDCl_3$): d 0.70 and 0.80 [two s, 6, $CH_2CH(CH_3)_2$], 1.07–1.40 [m, 3, $CH_2CH(CH_3)_2$], 3.07–3.43 (m, 2, $bCH_2$ $Trp^P$), 4.40–4.73 (m, 2, aCH Leu and aCH $Trp^P$), 4.83–5.03 (m, 2, $CH_2Ph$), 6.07–6.40 (two, m, 2, amide NH), 6.57–7.53 (m, 13, aromatics), 8.07 (bs, 1, NH of indole). Calculated for $C_{28}H_{32}N_3O_6P.1\ H_2O$: C, 60.48; H, 6.12; N, 7.56. Found C, 60.46; H, 5.99; N, 7.50%.

EXAMPLE 5

Inhibition of Adamalysin II

The enzyme Adamalysin II, isolated from venom of the species Crotalus Adamanteus and obtained in extremely pure form from the laboratory of Prof. L. F. Kress (Buffalo, N.Y., USA), was tested in its capacity of operating the scission of the fluorescent substratum 2-aminobenzoyl-ALA-GLY-LEU-ALA-4-nitrobenzylamide (of the Bachem firm). The production in time of fluorescent compounds was followed for 30 minutes, using as a detector a Perkin Elmer L 50B spectrofluorimeter, fixed at 320 m for the excitation and at 420 nm for the emission.

Results ($IC_{50}$ expresses the concentration of the compound capable of reducing by 50% the scission of the fluorescent subtratum):

TABLE I

| COMPOUND | $IC_{50}$ |
| --- | --- |
| Compound n.3a | $4 \times 10\text{-}7$ M |
| Compound n.3b | $2,2 \times 10\text{-}7$ M |
| Compound n.3d | $6,6 \times 10\text{-}7$ M |
| Compound n.3e | $5,5 \times 10\text{-}7$ M |
| Compound n.4 | $1,0 \times 10\text{-}6$ M |
| Compound n.3f | $1,0 \times 10\text{-}6$ M |
| Compound n.3c | $2,2 \times 10\text{-}5$ M |
| Compound n.9 | $7,2 \times 10\text{-}6$ M |

As can be seen in the reference table, all tested compounds result capable of inhibiting the enzyme, and some show remarkable power.

EXAMPLE 6

Inhibition of the human enzyme Gelatinase A (MMP-2)

The snythetized compounds were also tested on the enzyme of human orgin Gelatinase A, known also as MMP-2 (Matrix Metalloproteinase n. 2). The pure enzyme, extracted from human cultures and obtained from Pro. G. Murphy (Strangeways Labs., Cambridge, UK), was first activated with p-amino-mercuryacetate, and proteolytic activity was evidentiated with the use of an artificial fluorescent substratum MCA-PRO-LEU-GLY-LEU-DPA-ALA-ARG-NH2 (Strangeways Labs.), in spectrofluorimeter Perkin Elmer L 50B fixed at 328 nm for excitation and 393 nm for emission. To test inhibitory activity, synthetized compounds were incubated for 3 hours at room temperature in the presence of the enzyme, before adding the substratum.

The results, expressed qualitatively, are shown in the following table:

TABLE II

| COMPOUND | INHIBITION |
| --- | --- |
| Compound n.3a | Fair |
| Compound n.3b | Good |
| Compound n.3d | None |
| Compound n.3e | Fair |
| Compound n.4 | None |
| Compound n.3f | Fair |

TABLE II-continued

| COMPOUND | INHIBITION |
| --- | --- |
| Compound n.3c | Good |
| Compound n.9 | None |

EXAMAPLE 7

Inhibition of human enzyme Collagenase from neutrophiles (MMP-8)

The new synthetized derivatives were also tested on another zinc-dependent metalloproteinase of human orgin: the Collagenase from neutrophiles, also known as MMP-8 (Matrix Metalloproteinase N. 8). The pure enzyme extracted from human cell cultures and obtained from Prof. G. Murphy (Strangeways Labs., Cambridge, UK), was activated with p-aminomercuryacetate (2 hours at 37° C.), and enzymatic activity was followed by the spectrofluorimeter in the same way as described in the previous chapter.

The results, expressed qualitatively, are shown in the following table:

TABLE III

| COMPOUND | INHIBITION |
| --- | --- |
| Compound n.3a | Fair |
| Compound n.3b | Good |
| Compound n.3d | Fair |
| Compound n.3e | Fair |
| Compound n.4 | None |
| Compound n.3f | Good |
| Compound n.3c | Good |
| Compound n.9 | Fair |

What is claimed is:
1. Compound of formula:

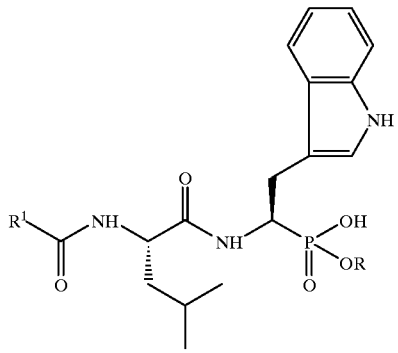

in which R is H, or $CH_2$—$C_6H_5$, and R' is a saturated or aromatic ring of five or six members, of which at least one is nitrogen, oxygen or sulphur.

2. Compound according to claim 1, in which R' is selected from the group consisting of :

R' =

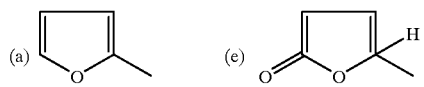

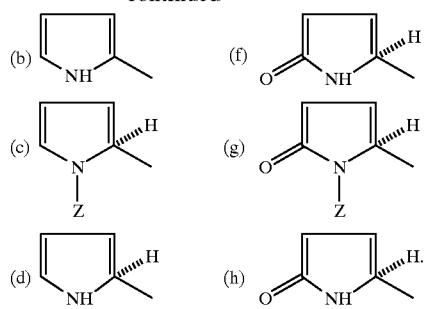

3. Pharmaceutical composition useful for therapy of human pathologies in whose pathogenic mechanism or in whose symptomatology an involvment of at least one zinc-dependent metalloproteinase has been proven, comprising as an active principle at least one of the compounds as claimed in claim 2, and a pharmaceutically compatible vehicle.

4. In a method of inhibiting enzymatic activity of at least one snake zinc-dependent metalloproteinase extracted from snake venoms belonging to the families Crotalidae and Viperidae, also called hemorrhagines, and/or at least one zinc-dependent metalloproteinase of human origin whose active site presents a three-dimensional structure analogous to that of said snake metalloproteinase, comprising
administering an inhibition-effective amount of an inhibitor of metalloproteinase to be a patient in need thereof suffering from a pathology in which the pathogenic mechanism or in which the symptomatology thereof has been shown to involve at least one zinc-dependent metalloproteinase, the improvement wherein
said inhibitor is a compound according to claim 2.

5. A method according to claim 4, in which said human metalloproteinase is ADAM.

6. A method according to claim 4, in which said metalloproteinase is Adamlysin II, Collagenase or Gelatinase A.

7. The compound of claim 1 for inhibiting enzymatic activity of at least on snake zinc-dependent metalloproteinase extracted from snake venoms belonging to the families Crotalidae and Viperidae, also called hemorrhagines, and/or at least one zinc-dependent metalloproteinase of human origin whose active site presents a three-dimensional structure analogous to that of said snake metalloproteinase.

8. A compund according to claim 7, in which said human metalloproteinases are ADAM.

9. A compound according to claim 7, in which said metalloproteinase is Adamalysin II, and/or Collagenase and Gelatinase A.

10. Pharmaceutical composition useful for therapy of human pathologies in whose pathogenic mechanism or in whose sympotomatology an involvement of at least one zinc-dependent metalloproteinase has been proved, comprising as an active principle at least one of the compounds as claimed in claim 1 and a pharmaceutically compatible vehicle.

* * * * *